US006927262B2

(12) United States Patent
Buzin et al.

(10) Patent No.: US 6,927,262 B2
(45) Date of Patent: Aug. 9, 2005

(54) BRIDGED BIPHOSPHOLES AND METALLOCENES PREPARED THEREFROM

(75) Inventors: Francois-Xavier Buzin, Paris (FR); Francois Nief, Anthony (FR); Francois Mathey, Paris (FR); Jean Malinge, Saint Genis Laval (FR); Eliane Deschamps, Palaiseau (FR); Bernard Deschamps, Palaiseau (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/466,434

(22) PCT Filed: Jan. 25, 2002

(86) PCT No.: PCT/FR02/00310

§ 371 (c)(1),
(2), (4) Date: Apr. 8, 2004

(87) PCT Pub. No.: WO02/059133

PCT Pub. Date: Aug. 1, 2002

(65) Prior Publication Data

US 2004/0260041 A1 Dec. 23, 2004

(30) Foreign Application Priority Data

Jan. 26, 2001 (FR) .......................................... 01 01088

(51) Int. Cl.$^7$ ................................................. C08F 4/16
(52) U.S. Cl. ...................... 526/161; 526/172; 526/126; 526/352; 526/348.6; 526/169; 556/14; 556/20; 556/21; 556/22; 556/23; 556/52; 502/103; 502/208; 502/210; 502/213; 568/12
(58) Field of Search .......................... 556/14, 20, 21, 556/22, 23, 52; 502/103, 208, 210, 213; 526/161, 169, 172, 126, 352, 348.6, 943, 941; 568/12

(56) References Cited

U.S. PATENT DOCUMENTS

| | | | | |
|---|---|---|---|---|
| 4,404,147 A | * | 9/1983 | de Lauzon et al. | 556/20 |
| 4,504,683 A | * | 3/1985 | Breque et al. | 568/12 |
| 5,434,116 A | * | 7/1995 | Sone et al. | 502/103 |
| 6,051,667 A | * | 4/2000 | von Haken Spence et al. | 526/127 |
| 6,124,487 A | * | 9/2000 | Spence et al. | 556/11 |
| 6,137,012 A | * | 10/2000 | Fagan et al. | 568/12 |
| 6,156,857 A | * | 12/2000 | Starzewski et al. | 526/161 |
| 6,172,169 B1 | | 1/2001 | Starzewski et al. | 526/161 |
| 6,174,974 B1 | | 1/2001 | Starzewski et al. | 526/161 |
| 6,191,241 B1 | | 2/2001 | Starzewski et al. | 526/161 |
| 6,232,413 B1 | | 5/2001 | Starzewski et al. | 526/134 |
| 6,350,903 B1 | * | 2/2002 | Fagan et al. | 562/12 |

FOREIGN PATENT DOCUMENTS

| | | | | |
|---|---|---|---|---|
| DE | 199 21 730 A1 | * | 11/2000 | C07C/45/50 |
| JP | 6-49121 A | * | 2/1994 | C08F/10/00 |
| JP | 11-80231 A | * | 3/1999 | C08F/4/642 |
| WO | WO 98/01485 | | 1/1998 | |
| WO | WO 98/41529 | | 9/1998 | |
| WO | WO 98/50392 | | 11/1998 | |
| WO | WO 98/50392 A1 | * | 11/1998 | C07F/9/6568 |
| WO | WO 00/69801 A1 | * | 11/2000 | C07C/45/50 |

OTHER PUBLICATIONS

Deschamps et al. Heteroatom Chemistry, 1991, 2(3), 377–383.*
Niemi et al. J. Chem. Soc., Perkin Trans. I, 2000, 1519–1528.*
JP 6–49121 (abstract in English).*
JP 11–80231 (abstract in English).*
de Boer et al. J. Mol. Catal. A, 1998, 155–165.*
Nief et al. Organometallics 1998, 7, 921–926.*
Nief et al. J. Organomet. Chem. 1990, 384,271–278.*
Gouygou et al. Organometallics 1997, 16, 1008–1015.*
E.J.M. de Boer et al., Journal of Molecular Catalysis A: Chemistry 128 (1998), 155–165.
F. Nief et al., J. of Organometallic Chemistry 384, 1990, p. 271–278.
Deschamps E., et al., "Stereochemistry and some synthetic uses of the heteroarylation of phospholes", Heteroatom Chemistry, vol. 2, No. 3, 1991, pp. 377–383.
Niemi T., et al., "The synthesis of stable 1,3,4–triphenylphospholes", Journal of the Chemical Society, Perkin Transactions 1, No. 10, May 21, 2000, pp. 1519–1528.
Gouygou M., et al., "Biphosphole: a C2 symmetry chiral bidentate ligand, synthesis and characterization of Nickel, Palladium, Platinum, and Rhodium complexes", Organometallics, vol. 16, No. 5, 1997, pp. 1008–1015.
Deschamps E., et al., "Synthesis and structure of a 1,1'–Diphospha(2) ferrocenophane" Organometallics, vol. 20, No. 8, 2001, pp. 1499–1500.
P.J. Fagan, et al., "Synthesis of Main Group Heterocycles by Metallacycle Transfer from Zirconium", Journal of the American Chemical Society, 1988, vol. 110, p. 2310–2312.

(Continued)

*Primary Examiner*—David W. Wu
*Assistant Examiner*—Rip A. Lee
(74) *Attorney, Agent, or Firm*—Smith, Gambrell and Russell, LLP

(57) ABSTRACT

The invention relates to novel bridged biphosphole ligands according to the general formula:

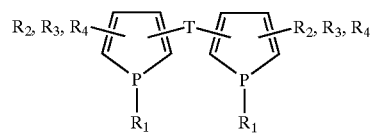

where $R^2$, $R^3$, $R^4$ are chosen from hydrogen, alkyl, aryl or silyl, $R^1$ is chosen from hydrogen, alkyl, aryl or halogen, $R^1$ possibly being replaced with a direct bond between the two phosphorus atoms and T is a divalent group. The invention also relates to metallocenes obtained from these ligands. These metallocenes are useful as catalytic components for the polymerization of olefins.

40 Claims, No Drawings

OTHER PUBLICATIONS

Stephen L. Buchwald, et al., "Selective, Zirocnium–Mediated Cross–Coupling of Alkynes: Synthesis of Isomerically Pure 1,3–Dienes and 1,4–Diiodo 1,3–Dienes", Journal of the American Chemical Society, 1989, vol. 111, p. 2870–2874.

Francois Mathey, et al., "Reduction–Complexation Des Sulfures De Phosphines Par Les Fer–Carbonyles", Journal of Organometallic Chemistry, vol. 136, (1977) pp. 241–249.

* cited by examiner

BRIDGED BIPHOSPHOLES AND METALLOCENES PREPARED THEREFROM

FIELD OF THE INVENTION

The subject of the present invention is novel catalysts for polymerizing olefins.

BACKGROUND OF THE INVENTION

Catalysts based on metallocenes are known. In these organometallic complexes, a metal atom is sandwiched between two cyclopentadienyl ligands. The synthesis, structure and properties of these complexes is described, for example, by Nicholas J. Long in "Metallocenes" published by Blackwell Science, 1998.

Ligands containing heteroatoms of the electron-donating type, such as phosphorus, are also known. Thus, cyclopentadienyl-derived ligands in which a carbon atom is replaced with a phosphorus atom are known. These ligands are denoted by the term "phospholyl".

Zirconium-based organometallic complexes comprising one or two substituted phospholyl ligands have been prepared. Their catalytic activity for the polymerization of ethylene is unsatisfactory (C. Janiak, U. Versteeg, K. C. H. Lange, R. Weimann and E. hahn, Journal of Organometallic Chemistry 501 (1995), 219–234).

Such substituted monophospholyls or biphospholyls of the $(R^1,R^2,R^3,R^4,C_4P)_2ZrCl_2$ type are also known, for Example from E. J. M. de Boer et al., Journal of Molecular Catalysis A: Chemistry 128 (1998), 155–165. Their catalytic activity with regard to the polymerization of propylene has been evaluated. Only complexes with a phospholyl ligand carrying at least one aryl substituent in a position adjacent to the phosphorus show a useful activity.

It is also known to use as catalyst complexes whose ligands are mutually bridged. In particular, application WO 98/41529 discloses bridged monophospholyl complexes of the [α-SiMe$_2$(3,4,5-trimethylphosphole, NtBu] TiCl$_2$ type. In such complexes, the metal is linked to a phosphorus atom and to a nitrogen atom.

Application WO 98/01485 discloses monophospholyls of the type bridged by a donor-acceptor type link between the phosphorus and the boron P→B:[2,3,4,5-pentamethylphosphole,Me$_2$B-Cp]TiCl$_2$.

DESCRIPTION OF THE INVENTION

Biphospholyls bridged to the phosphorus by metals are also known (F. Nief et al., J. of Organometallic Chemistry 384, 1990, p. 271–78).

Heteroatom Chemistry, vol. 2, No. 3, 1991, pp 377–383, Deschamps et al., discloses 1,1'-diphenyl-2,2'-thiophene-3,4,3',4' tetramethyl-biphosphole. There is no disclosure of any use of said compound.

J. Chem. Soc., Perkin Trans. 1, 2000, 1519–1528, pp 1519–1528, Niemi et al. discloses 1,1'-diphenyl-2,2'-vinylene-3,4,3',4' tetramethyl 5,5'dibromo-biphosphole. There is no disclosure of any use of said compound.

Organometallics, 1991, vol. 16, No. 5, pp 1008–1015, gouygou et al., discloses 1,1'-diphenyl-3,4,3',4' tetramethyl 2,2'-biphosphole znd its use for the synthesis of Ni, Pd and Pt-biphosphole complexes, these complexes being disclosed as being useful for enantioselective synthesis.

WO-A-9850392 discloses monophosphole compounds bridged with a cyclopentadienyle, indenyle ou fluorenyle cycle, optionally substituted. The disclosed application is alpha-olefines catalysis.

Organometallics, 2001, vol. 20, No. 8, pp 1499–1500, discloses synthesis of 1,1'-diphosphona[2]ferrocenophane, and as intermediates products the 2,2'-ethylene-3,4,3',4' tetramethyl-biphosphole and 1,1'-diphenyl-2,2'-ethylene-3,4,3',4' tetramethyl-biphosphole. Polymerization of diphosphona[2]ferrocenophane is disclosed. There is indeed no disclosure of any use of said intermediates products.

The object of the invention was therefore to produce novel catalysts in the field of metallocenes or the like for single-site catalysis.

This invention relates to novel compounds of the bridged biphospholyl type, to novel catalytic metallocene compositions based on these bridged biphospholes and to their intermediates and preparation processes. It also relates to processes for polymerizing olefins employing these catalytic components.

A first aspect of the invention therefore relates to bridged biphospholes that satisfy the general formula:

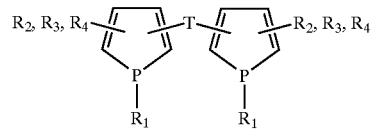

where:
$R^2$, $R^2$, $R^4$ are chosen from hydrogen, alkyl, aryl or silyl;
$R^1$ is chosen from hydrogen, alkyl, aryl or halogen, $R^1$ possibly being replaced by a direct bond between the two phosphorus atoms and T is a divalent group.

The divalent group T may include a ring, preferably an aromatic ring, in particular a benzene group.

Preferably, the divalent group T is a group satisfying the formula:

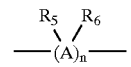

in which A is C, Si, ge or Sn;
$R^5$ and $R^6$ are, independently of each other, h, alkyl or aryl; and n is an integer from 1 to 10, preferably from 1 to 5.

Furthermore, if A is C, it will be possible for $R^5$ and $R^6$ to be connected together so as to form with A a saturated or unsaturated ring having from 3 to 12 carbon atoms.

In the present description, the term "alkyl" will be understood to mean a linear or branched hydrocarbon group containing 1 to 20 carbon atoms. The term "aryl" means an aryl group containing from 6 to 16 carbon atoms, possibly substituted with one or more alkyls containing from 1 to 20 carbon atoms. The term "alkoxy" is understood to mean a substituted or unsubstituted, linear or branched, ether group containing up to 20 carbon atoms. The term "silyl" will be understood to mean a hydrocarbon group containing silicon and up to 20 carbon atoms. The abbreviation "Cp" denotes the cyclopentadienyl ligand.

According to a preferred embodiment, A is a carbon atom and $R^5$ and $R^6$ are a hydrogen atom.

A value of n of 2 is particularly preferred, especially if A is a carbon atom and $R^5$ and $R^6$ are a hydrogen atom. The bridge T then takes the form of ethylene.

According to one embodiment, bridge T is free of heteroatoms, especially free of S, O and N.

According to one embodiment, bridge T is linear.

According to one embodiment, bridge T is saturated.

According to another embodiment, bridge T is unsaturated.

According to another embodiment, A is an Si, ge or Sn atom; $R^5$ and $R^6$ are alkyl or aryl groups. When A is Si, ge, Sn, n is preferably equal to 1.

According to one embodiment, the group T is located in the α position with respect to the phosphorus. The phosphorus atoms may then form a direct bond. According to another embodiment, the group T is located in the β position with respect to the phosphorus.

Preferably, $R^2$, $R^3$, $R^4$ are chosen from hydrogen, methyl or phenyl. $R^1$ is preferably phenyl or replaced with a direct bond between the phosphorus atoms.

Particularly preferred biphospholes according to the invention are 1,1'-diphenyl-2,2'-ethylene-4,5,4',5' tetramethyl-biphosphole and 2,2'-ethylene-4,5,4',5'-tetraphenyl-1,1'-biphospholyl.

The bridged biphospholes according to the invention may be prepared by various processes. In particular, they may be obtained by the following methods:

"Würtz-type coupling" method, giving the α bridge;

"bis(zirconacyclopentadiene)" method—this method allows α- or β-bridge compounds to be obtained depending on the diyne used; and "copper-mediated oxidative coupling" method, giving the α bridge.

According to a first embodiment, the invention provides a process for preparing an α- or β-bridged biphosphole comprising the steps of:

coupling in the presence of magnesium metal of two phosphole sulfides according to the following formula:

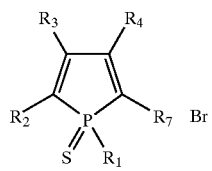

where $R^2$ to $R^4$ are chosen from hydrogen, alkyl, aryl or silyl;

$R^1$ is a group chosen from hydrogen, alkyl, aryl or halogen;

$R^7$ being chosen so as to form T after coupling; and reduction of the bridged disulfide into the bridged biphosphole.

Preferably, the bridged disulfide is isolated and purified before the reduction is carried out.

According to a second embodiment, the invention provides a process for preparing an α-bridged biphosphole comprising the steps of:

obtaining a bridged bis(alkenyl-chloro-zirconocene) by hydrozirconation of a diyne with chlorohydrurozirconocene;

converting the bridged bis(alkenyl-chloro-zirconocene) into a bridged bis(alkenyl-methyl-zirconocene);

decomposing the bridged bis(alkenyl-methyl-zirconocene) in the presence of an alkyne; and adding to the bridged bis(zirconacyclopentadiene) in solution an organodihalogenophosphine in order to obtain a bridged biphosphole.

According to a third embodiment, the invention provides a process for preparing a β-bridged biphosphole, comprising the steps of:

metallization of a complexed phosphole with a lithium alkylamide or silylamide into a complexed lithiomethylphosphole;

copper-mediated oxidative coupling of the complexed bridged biphosphole using cupric chloride;

partial decomplexation by the action of sulfur into a bridged biphosphole disulfide;

complete decomplexation by the action of cerium ammonium nitrate (CAN) into a bridged disulfide; and reduction to the biphosphole.

These bridged biphospholes may be used as transition metal ligands, in particular for the preparation of metallocenes.

A second aspect of the invention therefore relates to metallocenes obtained from these bridged biphospholes. The general formula of these metallocenes is:

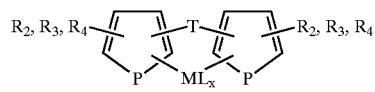

where $R^2$ to $R^4$ and T are defined as above, M is a metal of groups III, IV, V, VI, VIII or of the series of lanthanides or the actinides. Preferably, M is zirconium or titanium, L is a halogen, hydrogen, alkyl, aryl or alkoxy and x is an integer ranging from 1 to 3. If M is zirconium or titanium, x is preferably equal to 2.

Among these metallocenes, 1,1'-diphospha-2,2'-ethylene-4,5,4'5'-tetramethyl-dichlorozirconocene and 1,1'-diphospha-2,2'-ethylene-4,5,4',5'-tetraphenyldichlorozirconocene are particularly preferred.

The synthesis of the metallocene from the bridged biphosphole is carried out via the bridged biphospholyl dianion:

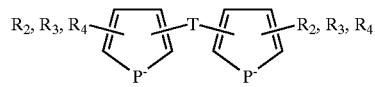

This dianion may be prepared by cutting the P—$R^1$ bond or by cutting the P—P bond. Preferably, this cutting is accomplished by an alkali metal, such as lithium, sodium or potassium.

The metallocene can then be obtained by reacting the bridged biphospholyl dianion with a metal halide using one of the methods known to those skilled in the art. The metallocene may thus be obtained by making the biphosphole with $R^1=SiR_3$ or $SnR_3$, R being an alkyl, react with a derivative of the metal M and preferably a halogenated derivative of $MX_4$ type.

According to one embodiment, the process for preparing a metallocene according to the invention then comprises the steps of:

conversion of a biphosphole according to the invention into a dianion by cutting the P—$R^1$ or P—P bond; and reacting the biphospholyl dianion with a halide of a metal from groups III, IV, V, VI, VIII or possibly of the series of lanthanides or actinides.

The metallocenes according to the invention can be used in particular as catalytic component for the polymerization of olefins.

The third aspect of the invention therefore relates to a catalytic component for polymerizing olefins. The metallocene may be employed by itself or in combination with other compounds. Preferably, the metallocene according to the invention is employed in combination with a cocatalyst.

Preferably the cocatalyst is an alumoxane (also called aluminoxane). These compounds may be linear, of formula:

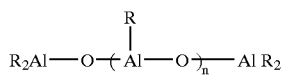

or cyclic, of formula:

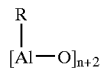

where, in the two formulae, R may be identical or different and represents an alkyl radical having from one to six carbon atoms, and n being an integer ranging from 2 to 40, preferably from 10 to 20. The aluminoxane may include R groups of different type. Moreover, it is possible to employ mixtures of these compounds.

Preferably, a linear aluminoxane is employed. Among linear aluminoxanes, methyl aluminoxane or "MAO" in which each R is methyl is preferred.

The use of other cocatalysts, such as ionic cocatalysts, is also possible. Among these cocatalysts, mention may be made of compounds containing cations such as trimethyl ammonium, tributyl ammonium, N,N-dimethylanilinium, carbonium, oxonium or sulfonium. The anions are preferably bulky and noncoordinating and may be, for example, tetraphenylborate, tetra(pentafluorophenyl) borate and anions containing more than one boron atom.

Moreover, it may be advantageous to employ compounds capable of trapping impurities, such as aluminum alkyls. Among aluminum alkyls, triisobutylaluminum (TiBA) is particularly preferred.

Moreover, the catalytic component may be employed in supported form, as is known to those skilled in the art. Such inert supports may be of an organic or inorganic nature, such as, for example, silica gel, $Al_2O_3$, $MgCl_2$ or polymers. It is possible to deposit the metallocene and the cocatalyst on the support in succession—firstly the metallocene and then the cocatalyst or vice versa or at the same time. Preferably, the cocatalyst is deposited on the support, then the metallocene.

The catalyst composition according to the invention may be prepared according to a process comprising the steps of:
impregnating a catalyst support with a cocatalyst; and, before, after or simultaneously,
impregnating this catalyst support with a metallocene according to the invention.

A fourth aspect of the invention is a process for polymerizing olefins, in which the catalytic component according to the invention is brought into contact with at least one olefin monomer under conditions of polymerization with a catalyst composition according to the invention.

The polymerization process may be a homopolymerization or copolymerization of one or more olefins, α-olefins, alkynes or diolefins as monomers. Preferably, this is a process for polymerizing ethylene and butene olefin monomers.

The polymerization processes are those conventionally used for polymerizing olefins, such as gas phase polymerization, suspension polymerization, at high pressure, or else solution polymerization.

The ligand, the compounds obtained therefrom and their preparation according to the invention will be described below in greater detail by means of a few examples.

Ligand

The ligand according to the invention is formed from two unsaturated phosphorous heterocycles called phospholes according to the IUPAC nomenclature in force, these being substituted with various monovalent groups and linked together by a divalent group, called hereafter a "bridge".

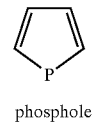

phosphole

The bridge may be located between the 2 position of one of the rings and the 2' position of the other ring (α bridge) or between the 3 position of one of the rings and the 3' position of the other ring (α bridge). This bridge is formed from a divalent group having one or more atoms (preferably 1 or 2) belonging to group IVb of the Periodic Table, preferably carbon or silicon, these being substituted with various monovalent groups.

The general formula of the ligand according to the invention, also called bridged biphosphole, satisfies one of the three following formulae. The numbering used is indicated below:

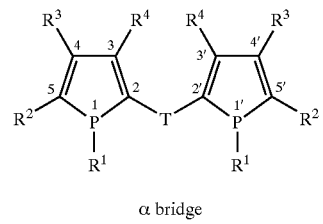

α bridge bridged biphospholes

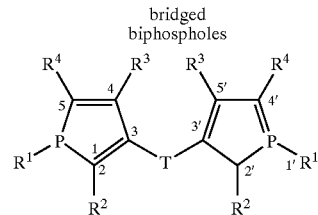

β bridge

A = C, Si, Ge, Sn

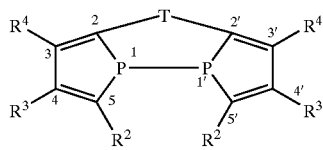

α bridge bridged 1,1'-biphospholyis

The groups $R^1$ to $R^6$ may be monovalent organic groups such as: hydrogen, alkyl, aryl, silyl; the group $R^1$ may also be a halogen. In addition, in the case of biphospholes bridged in the α position, there may be a direct bond between the two phosphorus atoms; these are then called bridged 1,1'-biphospholyls.

Synthesis of the Ligands

Three general methods for synthesizing the bridged biphospholes are described below.

(A) "Würtz Reaction"-Type Method

This method consists of Würtz-type oxidative coupling between two phosphole sulfides substituted in the α position by a brominated group.

This synthesis is explained by taking the Example of 2-bromomethylphosphole according to the scheme below; it is particularly well-suited for obtaining bridged biphospholes possessing an ethylene bridge in the α position. however, it is also possible to use this type of coupling for substituted ethylene bridges of the CR¹R² CR³R⁴ type.

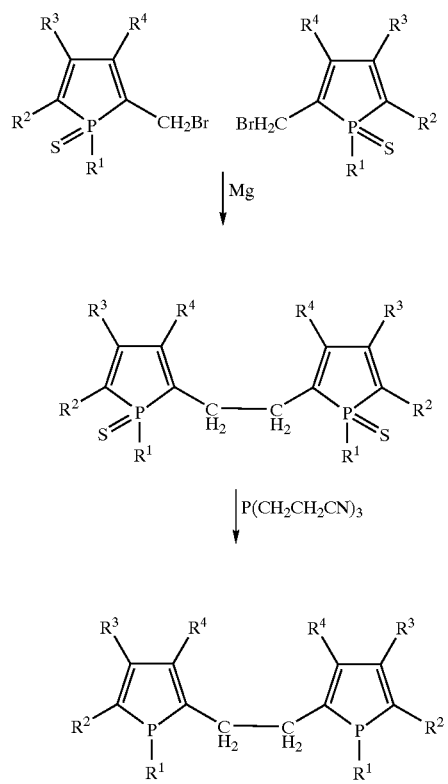

In this coupling reaction, two equivalents of a 2-bromomethylphosphole sulfide are brought into contact with 1 to 5 equivalents, preferably 5 equivalents, of magnesium metal in an ether solvent such as tetrahydrofuran (THF) or dimethoxyethane (DME), THF being preferred. The mixture is left to react at a temperature of between 25° C. and 40° C., preferably 35° C., for a time of greater than or equal to 2 hours, preferably 16 hours. The coupling product is then isolated and chromatographed on a silica gel column, with dichloromethane as eluent.

The bridged disulfide is then reduced to the bridged biphosphole. The reduction may be obtained by the action of a tertiary phosphine such as tributylphosphine or tri (cyanoethyl)phosphine, the latter being preferred. The reduction is preferably carried out at a temperature greater than or equal to 130° C., this being most easily achieved by reflux in xylene. The reaction is continued for a time of greater than or equal to 2 hours, preferably 16 hours. The bridged biphosphole obtained is purified by recrystallization in methanol.

The 2-bromomethylphosphole sulfide required by the coupling reaction may be conveniently obtained from 2-phosphole carboxaldehyde. The latter may be synthesized using the method described by E. Deschamps and F. Mathey, Bull. Soc. Chim. Fr. (1992), Vol. 129, p. 186.

The conversion of phosphole-2-carboxaldehyde to 2-bromomethylphosphole sulfide requires three elementary steps:

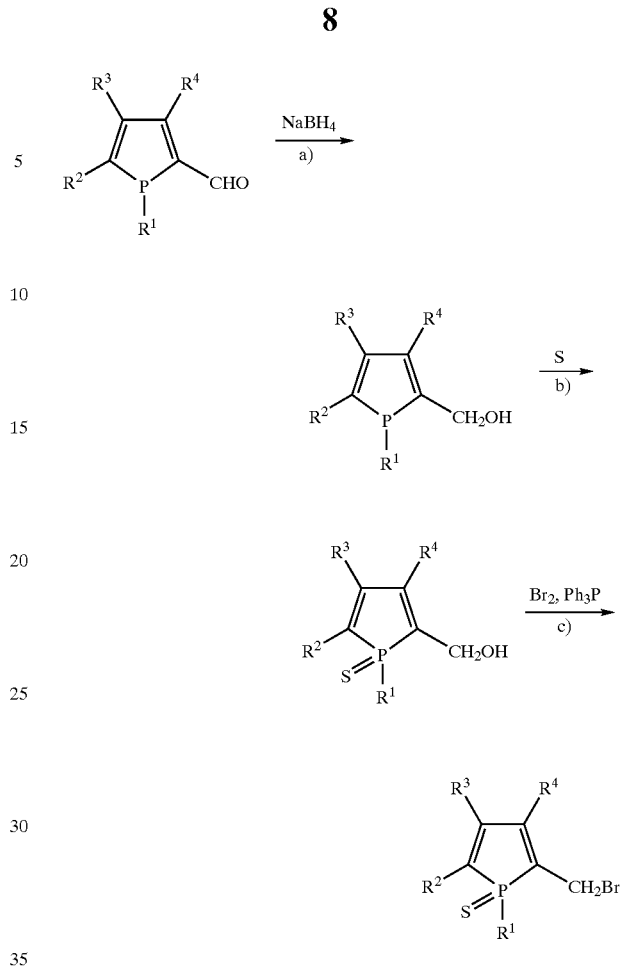

a) reduction of phosphole-2-carboxaldehyde to 2-hydroxymethylphosphole: added to phosphole-2-carboxaldehyde dissolved in an alcohol, preferably ethanol, is sodium borohydride, preferably one equivalent, at a temperature of 0° C. or below, preferably 0° C. The reaction mixture is brought back to 25° C. over 15 minutes; the 2-hydroxymethylphosphole thus obtained may be isolated, but it is preferably kept in solution for the next step;

b) passage from 2-hydroxymethylphosphole to 2-hydroxymethylphosphole sulfide: the raw solution from the previous step is cooled to 0° C. and added to this is one or more equivalents, preferably one equivalent, of elemental sulfur, then stirred for 15 minutes or longer, preferably 15 minutes and then brought back to room temperature over 15 minutes or longer, preferably 15 minutes. The solvent is evaporated and replaced with dichloromethane and then this phase is washed with a solution of sodium chloride to neutral pH, dried over magnesium sulfate and evaporated to dryness. The 2-hydroxymethylphosphole sulfide can then be purified by chromatography, but it is preferably used as such for the purpose of the next step;

c) conversion of 2-hydroxymethylphosphole sulfide to 2-bromomethylphosphole sulfide: the raw 2-hydroxymethylphosphole sulfide from the previous step is dissolved in dichloromethane in the presence of one equivalent of triphenylphosphine. A solution of one equivalent of dibromine in dichloromethane is then added drop by drop for ten minutes (preferably) or longer, the temperature of the reaction mixture being maintained between −20° C. and 0° C. (preferably 0° C.). The addition is stopped when the solution has a persistent yellow color, indicating that the dibromine is present in excess. The solution is washed with an aqueous sodium sulfite solution and evaporated to dryness under vacuum.

B) "Bridged bis(zirconacyclopentadiene)"-Type Method

In this method, the bridged biphospholes are obtained from bridged bis(zirconacyclopentadienes) by the action of an organodihalogenophosphine or a trihalogenophosphine in a zirconium-phosphorus metathesis reaction; this metathesis also produces dichlorozirconocene as a byproduct. This reaction was described for the first time by Fagan with a symmetrical and unbridged zirconacyclopentadiene (P. J. Fagan and W. A. Nugent, Journal of the American Chemical Society, 1988, Vol. 110, p. 2310).

The general principle of synthesizing these zirconacyclopentadienes is the oxidative coupling of two alkyne molecules about the zirconium. To synthesize bridged zirconacyclopentadienes, it is possible to adapt the published syntheses for unbridged zirconacyclopentadienes that use two different alkynes. In our case, it is recommended to effect the oxidative coupling using an alkyne and a diyne according to the following general scheme:

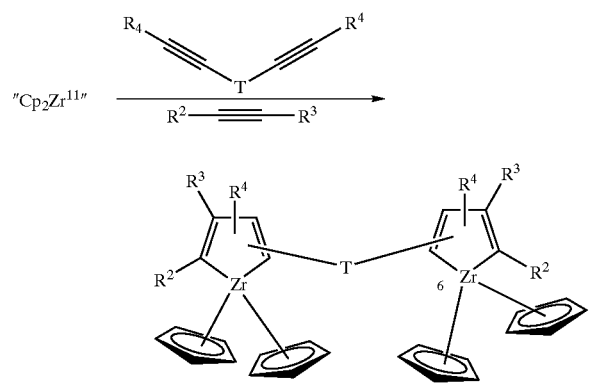

The difference in steric hindrance between the substituents on the acetylenes controls the regioselectivity of the coupling: bulky groups being placed in the α position with respect to the zirconium, the bridge being in the α position if the T group is bulkier than $R^4$ and in the β position otherwise.

As an example, the method that was chosen is based on a study by Buchwald et al. (S. Buchwald and R. B. Nelsen, Journal of the American Chemical Society, 1989, Vol. 111, p. 2870). The reaction mixture is as follows:

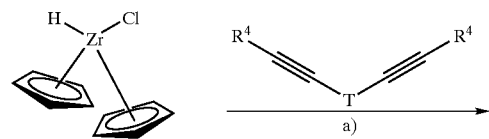

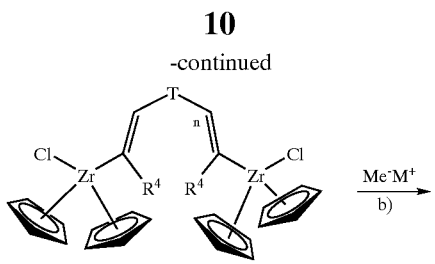

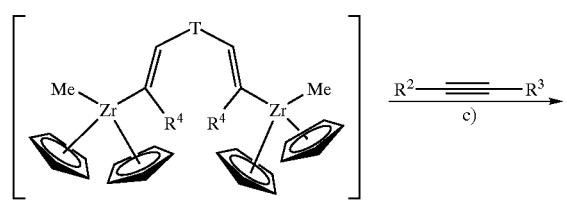

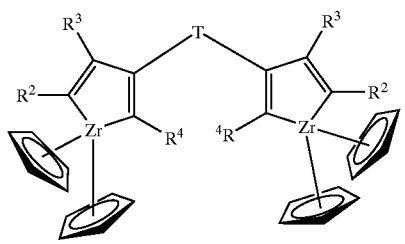

a) formation of a bridged bis(alkenyl-chloro-zirconocene) by hydrozirconation of a diyne with chorohydridozirconocene (also called Schwartz's reagent):

One equivalent of diyne and two equivalents of Schwartz's reagent are made to react in a solvent (THF or dichloromethane) for about one hour at a temperature of less than or equal to 0° C.; the reaction is terminated when the solution is homogeneous. The bridged bis(alkenyl-chloro-zirconocene) may be isolated, but it is preferably kept in solution for the purpose of the next step;

b) conversion of the bridged bis(alkenyl-chloro-zirconocene) to bridged bis(alkenyl-methyl-zirconocene): added to the raw solution from the previous step are two equivalents of methyllithium dissolved in ether at −78° C. (the solvent then being THF) or methyl magnesium bromide dissolved in ether at room temperature or below (the solvent being THF or dichloromethane) and two equivalents of an alkyne. The bridged bis(alkenyl-methyl-zirconocene) is not stable and cannot be isolated;

c) decomposition of the bridged bis(alkenyl-methyl-zirconocene) in the presence of an alkyne: the previous solution is kept at room temperature for at least two hours; over this time, the bridged bis(alkenyl-methyl-zirconocene) decomposes with evolution of methane and oxidative coupling takes place with the alkyne to give the bridged bis(zirconacyclopentadiene). This complex may be isolated, but it is preferably kept in solution for the purpose of synthesizing the bridged biphosphole by the Fagan method:

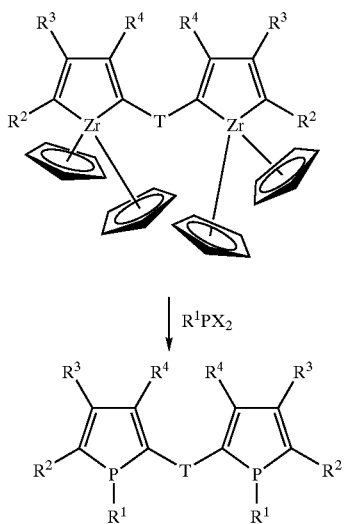

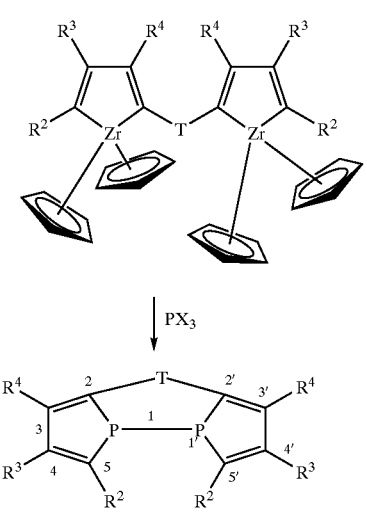

A stoichiometric quantity of organodihalogenophosphine is added to the bridged bis(zirconacyclopentadienes) dissolved in dichloromethane (preferably), an ether or a hydrocarbon, in a temperature range from 0° to 60° C. over times varying from 30 minutes to 24 h depending on the substitution scheme: when the group $R^2$ is bulky, the reaction time will be longer; it may also prove to be desirable, in this case to use a trihalogenophosphine, which is more electrophilic than a dihalogenophosphine; a bridged 1,1'-biphospholyl will then be obtained. This synthesis will be illustrated by the examples of 1,1'-diphenyl-2,2'-ethylene-4,5,4',5'-tetramethyl-biphosphole and 2,2'-ethylene-4,5,4',5'-tetraphenyl-1,1-biphospholyl.

C) Copper-Mediated Oxidative Coupling

This method consists of oxidative coupling, via cupric chloride, of a lithiomethylphosphole (a phosphole substituted with a —CH$_2$Li group), the latter being obtained from a phosphole carrying a methyl group by direct metallization with a strong base (lithium amide). This method will be very suitable for coupling in the β position; however, the scheme for substituting the initial phosphole preferably obeys the following relationships:

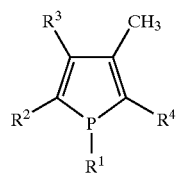

a) $R^3 = CH_3$, $R^2 = R^4 \neq$ alkyl
b) $R^2$, $R^3$, $R^4 \neq$ alkyl a) if $R^3$ is a methyl, the two substituents $R^2$ and $R^4$ are not alkyl groups and are furthermore identical;
b) if $R^3$ is not a methyl, the three substituents $R^2$, $R^3$ and $R^4$ are not alkyl groups, but may be different.

To increase the acidity of the methyl group in the 3 position of the phosphole and therefore to facilitate the direct metallization with a strong base, the two double bonds will be complexed by a (tricarbonyl)iron group and the lone pair of the phosphorus by a (tetracarbonyl)iron group, which also act as protective groups: these complexed phospholes may be synthesized as described by F. Mathey and g. Muller, Journal of Organometallic Chemistry, 1977, Vol. 136, p. 241).

The bridged biphospholes are obtained in five steps:

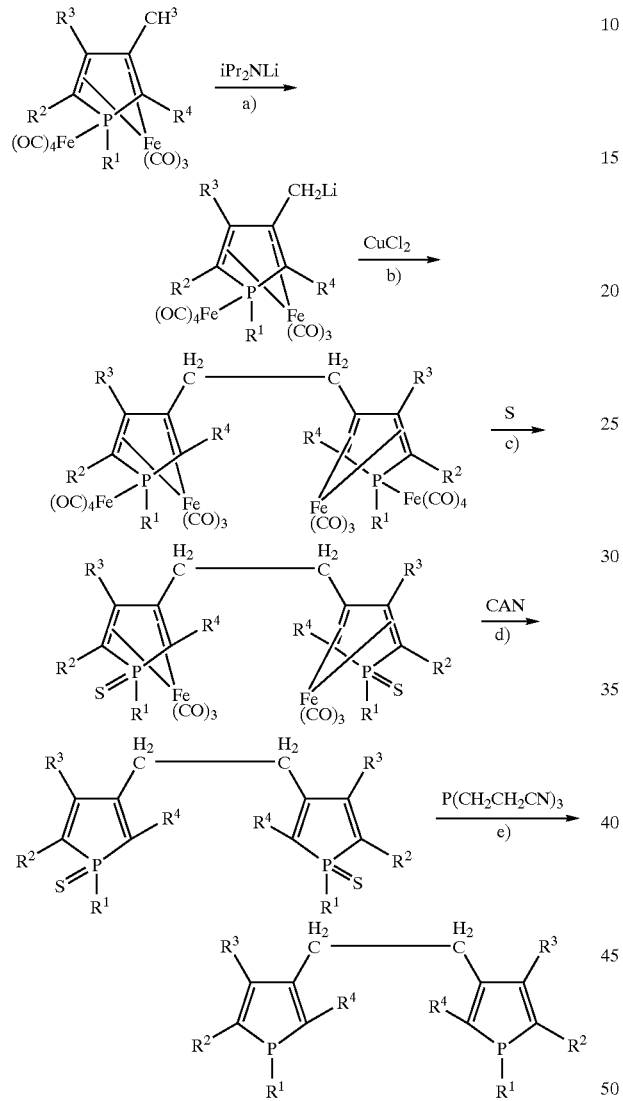

a) metallization of the complexed phosphole: added to the complexed phosphole, dissolved in THF, undergoes the addition at a temperature not exceeding −80° C. is one equivalent of a lithium alkylamide or silylamide (preferably lithium diisopropylamide); the addition lasts about ten minutes; the complexed lithiomethylphosphole obtained is kept dissolved at low temperature for the purpose of the next step;

b) actual copper-mediated oxidative coupling: one equivalent of cupric chloride is added at a temperature not exceeding −80° C. to the complexed lithiomethylphosphole obtained in the previous step. The reaction mixture is then brought back to room temperature over one hour, the solvent evaporated to dryness and the residue chromatographed on a silica column: a complexed bridged biphosphole is thus obtained;

c) partial decomplexation by the action of sulfur: the complexed bridged biphosphole obtained in the previous step is dissolved in toluene or xylene and 4 to 5 equivalents of elemental sulfur are added. The reaction mixture is taken to reflux from 1 to 2 hours, then evaporated to dryness and the residue chromatographed on a silica column. the product obtained is a complexed bridged biphosphole disulfide;

d) total decomplexation by the action of cerium ammonium nitrate (CAN): the complexed bridged biphosphole disulfide is dissolved in a 1/1 dichloromethane/isopropanol mixture and 4.5 equivalents of CAN are added. After 45 minutes of reaction, the reaction mixture is hydrolyzed and the solution is extracted with dichloromethane. The bridged biphosphole disulfide obtained is purified by chromatography on a silica column;

e) conversion of the bridged biphosphole disulfide into a bridged biphosphole: this reaction may be carried out under the same conditions as those described in A in the case of the α-bridged biphosphole.

Conversion into a Complex

The conversion of the ligand into a zirconium complex, denoted as "ansadiphosphadichloro-zirconocene" generally involves the following series of reactions:

1) cutting of the P—$R^1$ or P—P bonds of the ligand, preferably by an alkali metal—lithium, sodium or potassium—in a polar solvent such as, for example, tetrahydrofuran, with the formation of bridged biphospholyl dianions:

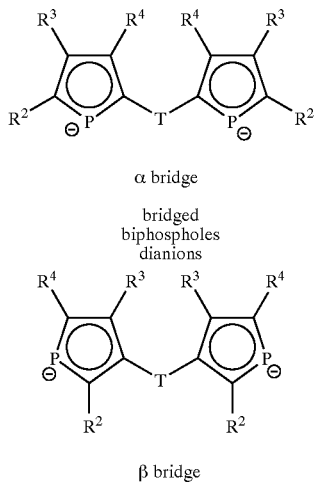

2) Reaction of these bridged biphospholyl dianions with zirconium tetrachloride to give the corresponding ansadiphosphadichlorozirconocenes:

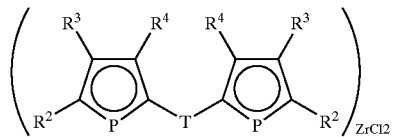

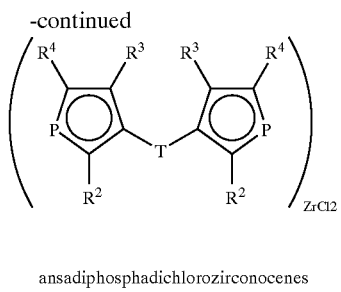

ansadiphosphadichlorozirconocenes

The general operating method for synthesizing the ansa-diphosphadichlorozirconocenes is not fundamentally different than that of the other diphosphadichlorozirconocenes—reference may be made to the methods described in WO 95/04087. This synthesis will be illustrated by the example of the preparation of 1,1'-diphospha-2,2'-ethylene-4,5,4',5'-tetramethyldichloro-zirconocene and 1,1'-diphospha-2,2'-ethylene-4,5,4',5'-tetraphenyldichlorozironocene.

The invention is illustrated by the following examples, without its scope being limited to them.

EXAMPLES

Examples of Synthesis of Ligands

Example 1

Synthesis of 1,1'-diphenyl-2,2'-ethylene-4,5,4'5'-tetramethylbiphosphole 5 ml of 1,5-hexadiyne (26.6 mmol) were added to a suspension of 13.74 g (53.2 mmol) of Schwartz's reagent in 100 ml of freshly distilled dichloromethane in a Schlenk tube under argon cooled to 0° C. The Schwartz's reagent gradually dissolved as it reacted over about one hour. The solution turned a clear light yellow.

2.87 g of 2-butyne (53.2 mmol) and then methylmagnesium bromide (53.2 mmol) were added, again at 0° C. A pale red solution was obtained, to which about twelve milliliters of THF were added in order to completely dissolve the grignard reagent. After a few minutes, the formation of insoluble magnesium salts again opacified the reaction mixture.

After stirring overnight at room temperature, dichlorophenylphosphine (7.2 ml, i.e. 53.2 mmol) were added to the reaction mixture cooled to 0° C.

Next, the reaction mixture was filtered and then the precipitate was washed with dichloromethane. After the combined organic phases had evaporated, the residue was extracted with toluene and then evaporated to dryness, the extraction/evaporation operation being repeated with ether and possibly with pentane.

The 5.11 g (48%) of 1,1'-diphenyl-2,2'-ethylene-4,5,4',5'-tetramethylbiphosphole thus obtained were recrystallized cold in methanol.

Example 2

Synthesis of 1,1'-diphospha-2,2'-ethylene-4,5,4'5'-tetramethyldichloro-zirconocene A solution of 480 mg (12 mmol) of 1,1'-diphenyl-2,2'-ethylene-4,5,4'5'-tetramethylbiphosphole in 20 ml of freshly distilled THF was brought into contact with 34 mg (48 mmol) of lithium pieces in a Schlenk tube under argon. The solution darkened and the presence of the bridged biphospholyl dianion was confirmed by $^{31}$P NMR. When there was no longer any biphosphole (after about one hour), about one hundred milligrams of aluminum trichloride (0.8 mmol) were added and the mixture left to stir for one quarter of an hour until complete dissolution.

The zirconium tetrachloride solvated by two molecules of tetrahydrofuran (ZrCl$_4$.2THF:450.5 mg; 12 mmol) was added as such to the bridged biphospholyl dianion solution. The complex formed immediately. Two diastereoisomers (2/3 of meso according to $^1$H NMR) were obtained. After the THF was evaporated, the bridged diphosphazirconocenes were washed with dichloromethane, then with toluene and, finally, recrystallized in pentane. 180 mg of 1,1'-diphospha-2,2'-ethylene-4,5,4',5'-tetramethyldichlorozirconocene were obtained in the form of yellow crystals (37%). No enrichment of one or other of the isomers was observed. In fact, an X-ray diffraction crystallographic study showed that these crystallize with the same unit cell.

Example 3

Synthesis of 2,2'-ethylene-4,5,4'5'-tetraphenyl-1,1'-biphospholyl 1.51 g of 1,5-hexadiyne (19.3 mmol) were added to a suspension of 10 g (38.6 mmol) of Schwartz's reagent in 120 ml of freshly distilled dichloromethane in a Schlenk tube under argon, cooled to 0° C. When the solution had become homogeneous, the solvent was evaporated and then the hydrozirconation product was taken up in tetrahydrofuran (120 ml) and the reaction mixture cooled −78° C. Methylmagnesium bromide (14.6 ml; 38.6 mmol) was added drop by drop and then the solution was stirred, cold, for a quarter of an hour. A small amount of trimethylsilyl chloride (0.21 ml; 1.7 mmol) was introduced to trap any unreacted grignard reagent and then, after one minute, diphenylacetylene (6.9 g; 38.6 mmol) dissolved in 5 ml of tetrahydrofuran was added. The cooling bath was removed and the solution was stirred at room temperature for 24 hours. The evolution of methane could be seen and the reaction mixture gradually turned an intense red color.

Phosphorus trichloride (3.38 ml; 38.6 mmol) was added at 0° C., and then the reaction mixture taken to room temperature over 16 hours. 1,1'-biphospholyl partly precipitated; the solution was filtered and the yellow solid collected was washed with hexane and optionally purified by succinct chromatography on silica gel with a dichloromethane/hexane (10/90) mixture as eluent. The filtrate was evaporated to dryness, taken up in dichloromethane, filtered over a glass frit and then chromatographed on silica gel. The excess diphenylacetylene was firstly eluted with hexane and then the 1,1'-biphospholyl was eluted with a dichloromethane/hexane (10/90) mixture. 3.27 g of 2,2'-ethylene-4,5,4',5'-tetraphenyl-1,1'-biphospholyl were thus obtained (35%). The 1,1'-biphospholyl was able to be recrystallized in a hexane/dichloromethane mixture by slowly evaporating the dichloromethane.

Example 4

Synthesis of 1,1'-diphospha-2,2'-ethylene-4,5,4'5'-tetraphenyldichlorozirconocene A solution—suspension of 2,2'-ethylene-4,5,4'5'-tetraphenyl-1,1'-biphospholyl (248 mg; 0.5 mmol) in tetrahydrofuran (6 ml)—was made to react with excess lithium at room temperature in a Schlenk tube under argon. The solution turned a deep red color as the phospholyl anion formed. When the 1,1'-biphospholyl had been entirely consumed, according to $^{31}$P NMR, the solution was added drop by drop to a suspension, cooled to 0° C., of ZrCl$_4$.2THF (189 mg; 0.5 mmol) in 9 ml of dry toluene. The reaction mixture was stirred at 0° C. for 20 minutes. The crude reaction mixture was stripped of its salts by filtration in dichloromethane. The diphosphadichlorozirconocene was obtained in the form of a pair of diastereoisomers (1:2 in favor of the meso-isomer according to $^{13}$C and $^{31}$P NMR), and its formation was accompanied by that of a small amount of 1,1'-biphospholyl (1:15). The complex partly precipitated when 5 ml of hexane were added to a solution of the mixture in 10 ml of toluene. The solution was filtered and the zirconocenes then crystallized slowly in the filtrate. The actual 1,1'-diphospha-2,2'-ethylene-4,5,4',5'-tetraphenyldichlorozirconocene was obtained with an 80% yield.

Examples of the Synthesis of Supported Catalysts

Example 5

Preparation of Catalytic Component C1

10 g of SYLOPOL 21-04 silica supplied by grace, that had been dehydrated beforehand by treatment at 200° C., were placed in a clean, dry 200 ml reactor purged with nitrogen then 50 g of a 10 wt % solution of MAO in toluene were added at room temperature. The mixture was taken to reflux for 4 h and then the toluene was removed by filtration. The solid S1 was washed twice with 50 ml of toluene and 50 ml of hexane, then dried at 50° C. under a dry nitrogen purge.

10 g of the solid S1 were placed under nitrogen in a clean, dry 500 ml reactor, followed by a suspension of 90 mg of the compound synthesized in Example 2 in 200 ml of dry hexane. The mixture was heated to 60° C. with stirring for 1 hour. The suspension was filtered and the solid washed twice with 100 ml of hexane at 45° C. The solid C1 obtained was dried at 65° C. It contained 0.26% Zr and 14.1% Al.

Example 6 (Comparative Example)

Preparation of Catalytic Component C2

The operating method for Example 5 was repeated, the 90 mg of compound synthesized in Example 2 being replaced with 100 mg of bis(2,3,4,5-tetramethylphospholyl) dichlorozirconocene synthesized according to the procedures known from the literature (see, for example, Boer et al. in J. Mol. Cat., A: Chem. 128(1998), 155–165 or Janiak et al. in J. Org. Chem. 501(1995), 219–224). The solid C2 thus obtained contains 0.2% Zr and 14.7% Al.

Examples of Polymerization

Example 7

Application of Catalytic Component C1 in the Copolymerization of Ethylene with Butene 1.4 bar of butene and 13.5 bar of ethylene were introduced at 75° C. into an 8-1 spherical polymerization reactor, provided with stirring and with temperature regulation, and containing 100 g of polymer produced during a prior trial carried out under the same conditions. Next, 110 mg of TiBA and 100 mg of catalytic component were injected via an airlock and via the thrust of pressurized dry nitrogen. The total pressure in the reactor was kept at 21 bar absolute for 4 hours with stirring, feeding the reactor continuously with a mixture of ethylene and butene in a butene/ethylene molar ratio of 0.046. After 4 hours, the polymer was isolated and weighed. The productivity determined by weighing the polymer was 2800 g of PEBdL/g/catalyst. The melt index under 2.16 kg (MI$_2$) was not measurable, the polymer being too viscous, the density was 0.930 and the butene content of the polymer was 1.3% by weight.

Example 8

This Example was produced under the same conditions, but with catalytic compound C1 substituted with component C2

Example 7 illustrates the invention; Example 8 is comparative.

The results of the evaluation of the ethylene-butene copolymerization catalysts are given in the table below.

| Catalyst | Productivity (g/g$_{cat}$) | Productivity (g/g$_{Zr}$ × 10$^{-6}$) | MI | D | % Butene |
|---|---|---|---|---|---|
| C1 | 2800 | 1.400 | nm* | 0.930 | 1.3 |
| C2 (comparative) | 330 | 0.165 | / | / | / |

*not measurable as the polymer viscosity was too high.

It may be seen that, for ethylene/butene copolymerization, the activities obtained are better in the case of the bridged biphosphole C1 compared with an unbridged biphosphole (C2).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. A bridged biphosphole according to the formula:

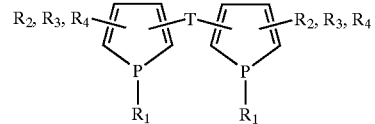

where:
R$^2$, R$^3$, R$^4$ are selected from hydrogen, alkyl, aryl or silyl;
R$^1$ is selected from hydrogen, alkyl, aryl or halogen, R$^1$ possibly being replaced by a direct bond between the two phosphorus atoms; and
T is a divalent group with the exclusion of the component 1,1'-diphenyl-2,2'-thiophene-3,4,3',4'tetramethylbiphosphole.

2. The bridged biphosphole as claimed in claim 1, wherein the divalent group T is a group according to the formula:

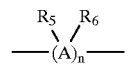

in which A is C, Si, Ge or Sn;
R$^5$ and R$^6$ are, independently of each other, H, alkyl or aryl; and n is an integer from 1 to 10.

3. The bridged biphosphole as claimed in claim 2, wherein A is a carbon atom and $R^5$ and $R^6$ are a hydrogen atom and n is equal to 2.

4. The bridged biphosphole as claimed in claim 2, wherein A is an Si, Ge or Sn atom and $R^5$ and $R^6$ are alkyl or aryl groups.

5. The bridged biphosphole as claimed in claim 2, wherein A is Si, Ge or Sn and n is equal to 1.

6. The bridged biphosphole as claimed in claim 1, wherein the divalent group T includes a ring.

7. The bridged biphosphole as claimed in claim 6, wherein the ring is an aromatic ring.

8. The bridged biphosphole as claimed in claim 7, wherein the aromatic ring is a benzene ring.

9. The bridged biphosphole as claimed in claim 1, wherein the group T is located in the α position with respect to the phosphorus.

10. The bridged biphosphole as claimed in claim 9, wherein the phosphorus atoms form a direct bond.

11. The bridged biphosphole as claimed in claim 1, wherein the group T is located in the β position with respect to the phosphorus.

12. The bridged biphosphole as claimed in claim 1, wherein $R^2$, $R^3$, $R^4$, are selected from hydrogen, methyl or phenyl.

13. The bridged biphosphole as claimed in claim 1, wherein $R^1$ is phenyl or is replaced with a direct bond between the phosphorus atoms.

14. The bridged biphosphole as claimed in claim 1, wherein the biphosphole is selected from 1,1'-diphenyl-2,2'-ethylene-4,5,4',5'tetramethyl-biphosphole and 2,2'-ethylene-4,5,4',5'-tetraphenyl-1,1'-biphospholyl.

15. A process for preparing a bridged biphosphole as claimed in claim 1, comprising:
coupling in the presence of magnesium metal of two phosphole sulfides according to the following formula:

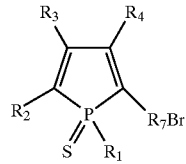

where:
$R^2$ to $R^4$ are selected from hydrogen, alkyl, aryl or silyl;
$R^1$ is a group selected from hydrogen, alkyl, aryl or halogen;
$R^7$ is selected to form T after coupling; and
reduction of the bridged disulfide obtained into the bridged biphosphole.

16. A process for preparing a bridged biphosphole as claimed in claim 1, comprising:
obtaining a bridged bis(alkenyl-chloro-zirconocene) by hydrozirconation of a diyne with chlorohydrurozirconocene;
converting the bridged bis(alkenyl-chloro-zirconocene) into a bridged bis(alkenyl-methyl-zirconocene);
decomposing the bridged bis(alkenyl-methyl-zirconocene) in the presence of an alkyne; and
adding to the bridged bis(zirconacyclopentadiene) in solution an organodihalogenophosphine to obtain a bridged 1,1'-biphospholyl.

17. A process for preparing a bridged biphosphole as claimed in claim 11, comprising:
metallization of a complexed phosphole with a lithium alkylamide or silylamide into a complexed lithiomethyiphosphole;
copper-mediated oxidative coupling of the complexed bridged biphosphole using cupric chloride;
partial decomplexation by the action of sulfur into a bridged biphosphole disulfide;
complete decomplexation by the action of cerium ammonium nitrate (CAN) into a bridged disulfide; and
reduction to the biphosphole.

18. A metallocene according to the formula:

where:
$R^2$, $R^3$, and $R^4$ are selected from hydrogen, alkyl, aryl or silyl;
T is a divalent group;
M is a metal from Groups III, IV, V, VI, VIII or from the series of lanthanides or actinides;
L is a halogen, a hydrogen, an alkyl, an aryl or an alkoxy; and
x is an integer ranging from 1 to 3.

19. The metallocene as claimed in claim 18, wherein the divalent group T is a group according to the formula:

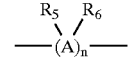

in which A is C, Si, Ge or Sn;
$R^5$ and $R^6$ are, independently of each other, H, alkyl or aryl; and n is an integer from 1 to 10.

20. The metallocene as claimed in claim 19, wherein A is a carbon atom and $R^5$ and $R^6$ are a hydrogen atom and n is equal to 2.

21. The metallocene as claimed in claim 19 wherein A is an Si, Ge or Sn atom and $R^5$ and $R^6$ are alkyl or aryl groups.

22. The metallocene as claimed in claim 19, wherein A is Si, Ge or Sn and n is equal to 1.

23. The metallocene as claimed in claim 18, wherein M is zirconium or titanium and x is equal to 2.

24. The metallocene as claimed in claim 23, wherein it is 1,1'-diphospha-2,2'-ethylene-4,5,4',5'-tetramethyl-dichlorozirconocene.

25. A process for preparing a metallocene as claimed in claim 18, comprising:
conversion of a biphosphole according to the general formula:

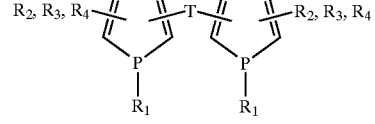

where:
$R^2$, $R^3$, $R^4$ are chosen from hydrogen, alkyl, aryl or silyl;
$R_1$ is chosen from hydrogen, alkyl, aryl or halogen, $R^1$ possibly being replaced by a direct bond between the two phosphorus atoms; and T is a divalent group;

in which $R^2$, $R^3$, $R^4$ and T are as claimed in claim 1, into a dianion by cutting the P—$R^1$ or P—P bond; and reacting the biphospholyl dianion with a halide of a metal from Groups III, IV, V, VI, VIII or optionally of the series of lanthanides or actinides.

26. A process as claimed in claim 25, wherein the bridged biphosphole $R^1$ is a phenyl or is replaced by a direct bond between the two phosphorus atoms.

27. A catalyst composition comprising a metallocene as claimed in claim 18.

28. The catalyst composition as claimed in claim 27, further comprising an aluminoxane and/or a substantially noncoordinating anion as cocatalyst.

29. The catalyst composition as claimed in claim 27, supported on an inert catalyst support.

30. A process for preparing the catalyst composition as claimed in claim 27, comprising:

impregnating a catalyst support with a cocatalyst; and, before, after or simultaneously, impregnating this catalyst support with a metallocene as claimed in claim 18.

31. A process for polymerizing olefins, comprising bringing at least one olefin monomer under polymerization conditions into contact with a catalyst composition as claimed in claim 27.

32. The process as claimed in claim 31, wherein the olefin monomers are ethylene and butene.

33. The metallocene as claimed in claim 18, wherein the divalent group T includes a ring.

34. The metallocene as claimed in claim 33, wherein the ring is an aromatic ring.

35. The metallocene as claimed in claim 34, wherein the aromatic ring is a benzene ring.

36. The metallocene as claimed in claim 18, wherein the group T is located in the α position with respect to the phosphorus.

37. The metallocene as claimed in claim 36, wherein the phosphorus atoms form a direct bond.

38. The metallocene as claimed in claim 18, wherein the group T is located in the β position with respect to the phosphorus.

39. The metallocene as claimed in claim 18, wherein $R^2$, $R^3$, $R^4$, are selected from hydrogen, methyl or phenyl.

40. A process for preparing a bridged biphosphole as claimed in 1,1'-diphenyl-2,2'-thiophene-3,4,3',4'tetramethylbiphosphole, comprising:

obtaining a bridged bis(alkenyl-chloro-zirconocene) by hydrozirconation of a diyne with chlorohydrurozirconocene;

converting the bridged bis(alkenyl-chloro-zirconocene) into a bridged bis(alkenyl-methyl-zirconocene);

decomposing the bridged bis(alkenyl-methyl-zirconocene) in the presence of an alkyne; and adding to the bridged bis(zirconacyclopentadiene) in solution an organodihalogenophosphine in order to obtain a bridged 1,1'-biphospholyl.

\* \* \* \* \*